(12) United States Patent
Salo et al.

(10) Patent No.: US 7,941,216 B2
(45) Date of Patent: May 10, 2011

(54) METHOD AND DEVICE FOR TREATING MYOCARDIAL ISCHEMIA

(75) Inventors: Rodney W. Salo, Fridley, MN (US); Allan C. Shuros, St. Paul, MN (US); Tamara Colette Baynham, Blaine, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 268 days.

(21) Appl. No.: 11/561,049

(22) Filed: Nov. 17, 2006

(65) Prior Publication Data

US 2008/0119904 A1 May 22, 2008

(51) Int. Cl.
*A61N 1/362* (2006.01)

(52) U.S. Cl. .............................. 607/9; 607/59

(58) Field of Classification Search .............. 607/9
See application file for complete search history.

(56) References Cited

U.S. PATENT DOCUMENTS

| | | | |
|---|---|---|---|
| 4,945,909 A * | 8/1990 | Fearnot et al. ............... | 607/14 |
| 5,372,607 A * | 12/1994 | Stone et al. .................. | 607/30 |
| 5,487,752 A | 1/1996 | Salo et al. | |
| 5,919,209 A * | 7/1999 | Schouten ..................... | 607/2 |
| 6,498,950 B1 | 12/2002 | Bradley | |
| 6,580,946 B2 | 6/2003 | Struble | |
| 6,628,988 B2 | 9/2003 | Kramer et al. | |
| 6,865,420 B1 * | 3/2005 | Kroll .............................. | 607/25 |
| 6,885,890 B2 * | 4/2005 | Spinelli et al. ............... | 607/14 |
| 6,915,160 B2 | 7/2005 | Auricchio et al. | |
| 6,937,901 B2 * | 8/2005 | Zhu et al. ..................... | 607/27 |
| 6,950,701 B2 * | 9/2005 | Begemann et al. ........... | 607/9 |
| 6,965,797 B2 | 11/2005 | Pastore et al. | |
| 6,973,349 B2 | 12/2005 | Salo | |
| 7,065,405 B2 * | 6/2006 | Pastore et al. ................ | 607/9 |
| 7,194,307 B2 | 3/2007 | Salo et al. | |
| 7,450,988 B2 * | 11/2008 | Ross et al. .................... | 607/9 |
| 2002/0087694 A1 | 7/2002 | Daoud et al. | |
| 2004/0133247 A1 | 7/2004 | Stahmann et al. | |
| 2004/0215262 A1 * | 10/2004 | Ferek-Petric ................ | 607/17 |
| 2004/0260348 A1 | 12/2004 | Bakken et al. | |
| 2005/0177195 A1 * | 8/2005 | Salo ............................. | 607/11 |
| 2006/0074189 A1 | 4/2006 | Gammie et al. | |
| 2006/0287684 A1 | 12/2006 | Baynham et al. | |

(Continued)

FOREIGN PATENT DOCUMENTS

WO    WO-01/76689 A2    10/2001

(Continued)

OTHER PUBLICATIONS

Dhalla et al. Myocardial Ischemia and Preconditioning. Springer, 2003. ISBN 1402071957, 9781402071959. pp. 423-429.*

(Continued)

*Primary Examiner* — Carl H Layno
*Assistant Examiner* — Jeremiah T Kimball
(74) *Attorney, Agent, or Firm* — Schwegman, Lundberg & Woessner, P.A.

(57) ABSTRACT

A method and device for treating myocardial ischemia are described in which the stress experienced by a myocardial region identified as vulnerable to becoming ischemic is varied with pre-excitation pacing. In an unloading mode, pacing is applied in proximity to the vulnerable region to reduce stress and the metabolic demand of the region. In a loading mode, pacing is applied to a region remote from the vulnerable region in order to produce a conditioning effect.

19 Claims, 4 Drawing Sheets

U.S. PATENT DOCUMENTS

| | | |
|---|---|---|
| 2008/0114407 A1 | 5/2008 | Pastore et al. |
| 2008/0114408 A1 | 5/2008 | Shuros et al. |

FOREIGN PATENT DOCUMENTS

| | | |
|---|---|---|
| WO | WO-0176689 A2 | 10/2001 |
| WO | WO-02/087694 A1 | 11/2002 |
| WO | WO 02087694 A1 * | 11/2002 |
| WO | WO-2006/074189 A1 | 7/2006 |
| WO | WO 2006074189 A1 * | 7/2006 |
| WO | WO-2008063536 A1 | 5/2008 |
| WO | WO-2008079370 A1 | 7/2008 |

OTHER PUBLICATIONS

"PCT Application No. PCT/US2007/023996, International Search Report mailed Apr. 1, 2008", 4 pgs.

"PCT Application No. PCT/US2007/023996, Written Opinion mailed Apr. 1, 2008", 6 pgs.

Sathaye, A. S., et al., "Post-MI Pacing With Autocapture Function", U.S. Appl. No. 11/427,517, filed Jun. 29, 2006.

"PCT Application No. PCT/US2007/026235, International Search Report mailed Apr. 7, 2008", 4 pgs.

"PCT Application No. PCT/US2007/026235, Written Opinion mailed Apr. 7, 2008", 8 pgs.

"U.S. Appl. No. 11/615,383, Final Office Action mailed Mar. 12, 2010", 15 pgs.

"U.S. Appl. No. 11/615,383, Notice of Non-Compliant Amendment mailed Sep. 18, 2009", 3 pgs.

"U.S. Appl. No. 11/615,383, Response filed Aug. 12, 2010 to Final Office Action mailed Mar. 12, 2010", 9 pgs.

"Australian Application Serial No. 2007322056, First Examiner Report mailed Sep. 6, 2010", 3 pgs.

"Australian Application Serial No. 2007338688, First Examiner Report mailed May 27, 2010", 4 Pgs.

"European Application Serial No. 07853460.9, Office Action mailed Aug. 6, 2010", 5 pgs.

* cited by examiner

METHOD AND DEVICE FOR TREATING MYOCARDIAL ISCHEMIA

RELATED CASES

This application is related to U.S. Pat. Nos. 6,628,988, 6,973,349, 6,915,160, and 6,965,797 and to U.S. patent application Ser. Nos. 11/427,517, filed on Jun. 29, 2006 and 11/541,837, filed on Oct. 2, 2006, all of which are hereby incorporated by reference in their entirety.

FIELD OF THE INVENTION

This invention pertains to cardiac rhythm management devices such as pacemakers and other implantable devices.

BACKGROUND

Myocardial ischemia refers to a condition in which the blood supply to a region of myocardium (i.e., heart muscle) becomes so compromised that the region is not supplied with adequate oxygen for oxidative metabolism. Ischemia, as opposed to hypoxia without any reduction in perfusion, is also accompanied by reduced removal of metabolic by-products. The heart is an aerobic organ that generates energy almost exclusively from the oxidation of substrates with oxygen delivered by the blood. It can develop only a small oxygen debt and is therefore extremely sensitive to disruptions in blood supply. Myocardial ischemia occurs when there is an imbalance between oxygen supply and demand as a result of increased myocardial oxygen demand, reduced myocardial oxygen supply, or both. Myocardial ischemia causes many patients to experience chest pain or discomfort, referred to as angina pectoris. Angina pectoris can serve as a useful warning of insufficient myocardial perfusion that can lead to the more serious situation such as a heart attack or cardiac arrhythmia.

Coronary artery disease (CAD) occurs when the coronary arteries that supply blood to the myocardium become hardened and narrowed due to the buildup of atherosclerotic plaque. An atherosclerotic plaque is the site of an inflammatory reaction within the wall of an artery and is made up of a core containing lipid and inflammatory cells surrounded by a connective tissue capsule. A myocardial infarction (MI), or heart attack, occurs when atherosclerotic plaque within a coronary artery ruptures and leads to the clotting of blood (thrombosis) within the artery by exposing the highly thrombogenic lipid core of the plaque to the blood. The complete or nearly complete obstruction to coronary blood flow can damage a substantial area of heart tissue and cause sudden death, usually due to an abnormal heart rhythm that prevents effective pumping.

In the presence of coronary obstruction due to CAD, an increase in myocardial oxygen requirements brought about by, for example, physical exertion or emotional distress, can cause a temporary imbalance in oxygen supply and demand. Such demand ischemia can cause what is called exertional anginal or chronic stable angina. In other situations, an imbalance can occur acutely due to a sudden reduction in blood flow, sometimes referred to as supply ischemia. An acute blood flow disruption may be secondary to a coronary vasospasm, causing what is called unstable angina. As noted above, an acute blood flow disruption can also result from coronary thrombosis, causing an MI. Myocardial ischemia often results from both an increase in oxygen demand and a reduction in supply.

DETAILED DESCRIPTION

Figure 1:
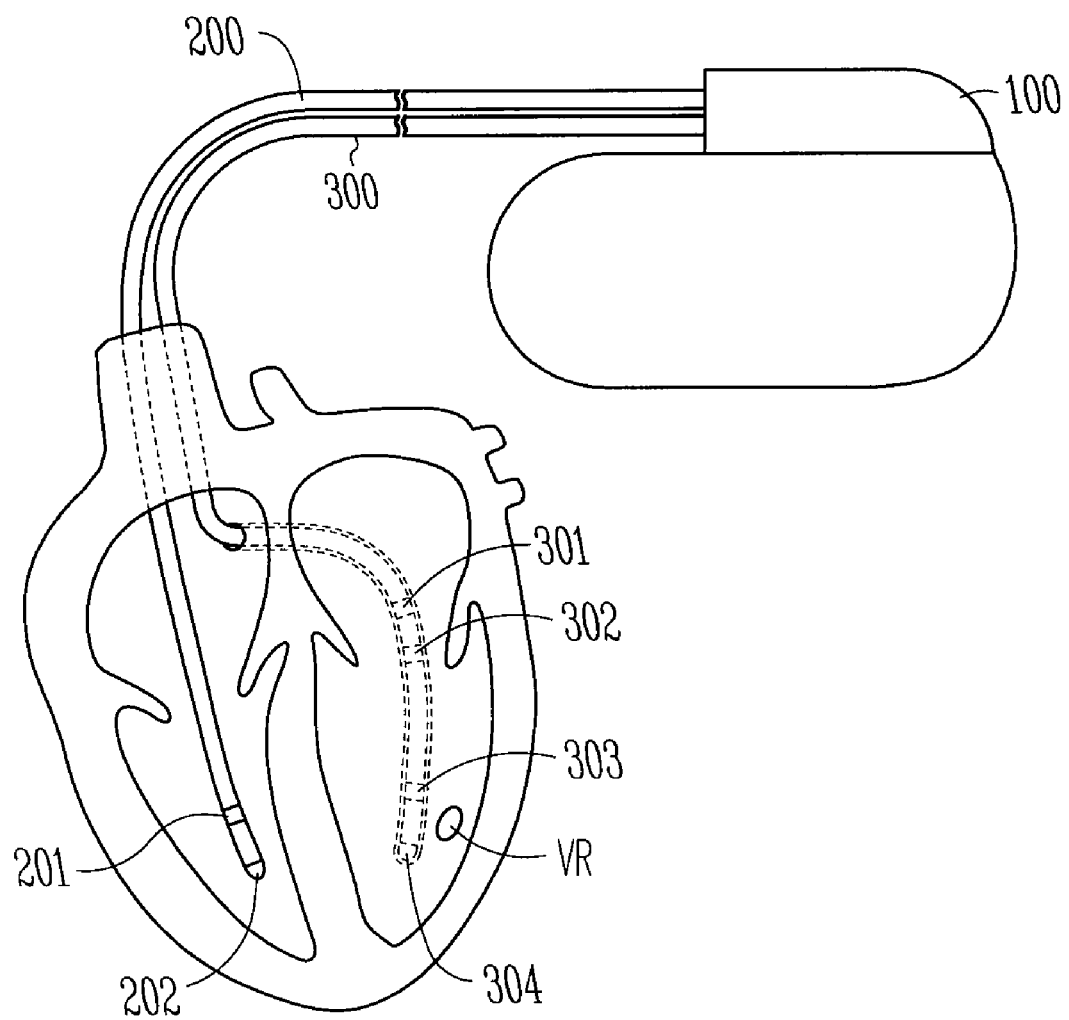
FIG. 1 illustrates the physical configuration of an exemplary pacing device.

Myocardial ischemia is usually treated with pharmacological agents that act to either increase myocardial perfusion or reduce myocardial oxygen demand. Surgical revascularization procedures may also be performed to increase blood supply. Described herein is an alternative intervention for treating myocardial ischemia that employs appropriately timed and located pacing pulses such as may be delivered by an implantable pacing device.

Mechanical Effects of Pacing Therapy

When the ventricles are stimulated to contract by a pacing pulse applied through an electrode located at a particular pacing site, the excitation spreads from the pacing site by conduction through the myocardium. This is different from the normal physiological situation, where the spread of excitation to the ventricles from the AV node makes use of the heart's specialized conduction system made up of Purkinje fibers which allows a rapid and synchronous excitation of the entire ventricular myocardium. The excitation resulting from a pacing pulse, on the other hand, produces a relatively asynchronous contraction due to the slower velocity at which excitation is conducted from the pacing site to the rest of the myocardium. Regions of the myocardium located more distally from the pacing site are thus excited later than regions proximal to the pacing site as compared with an intrinsic contraction. As explained below, this results in a re-distribution of myocardial wall stress.

The degree of tension on a muscle fiber before it contracts is termed the preload, while the degree of tension on a muscle fiber as it contracts is termed the afterload. Increasing the preload stretches a muscle fiber and also increases its maximum tension and velocity of shortening during contraction. With respect to the heart, the preload of a particular myocardial region is the myocardial wall stress at the end of diastole due to end-diastolic pressure and the forces applied by adjacent regions. The afterload of a myocardial region is the myocardial wall stress during systole due to the pressure load that the heart must pump against. When a myocardial region contracts late relative to other regions, the contraction of those other regions stretches the later contracting region and increases its preloading, thus causing an increase in the contractile force generated by the region. Conversely, a myocardial region that contracts earlier relative to other regions experiences decreased preloading and generates less contractile force. Because pressure within the ventricles rises rapidly from a diastolic to a systolic value as blood is pumped out into the aorta and pulmonary arteries, the parts of the ventricles that contract earlier during systole do so against a lower afterload than do parts of the ventricles contracting later. Delivery of a pacing pulse to a ventricular region makes that region contract earlier than other parts of the ventricle. The paced region will therefore be subjected to both a decreased preload and afterload which decreases the mechanical stress experienced by the region relative to other regions during systolic contraction. A region remote from the paced region on the other hand, will experience increased mechanical stress.

Pre-Excitation Pacing to Treat Myocardial Ischemia

All but a small fraction of the total amount of oxygen consumed by the myocardium is for the purpose of active muscular contraction during systole, and the oxygen demand of a particular myocardial region increases with increasing systolic wall stress. Causing a particular myocardial region to contract earlier relative to other regions will thus lessen its metabolic demands and the degree of any ischemia that may be present. In order to cause early contraction and lessened stress to a myocardial region vulnerable to becoming ischemic, electro-stimulatory pacing pulses may be delivered to one or more sites in or around the vulnerable region in a manner that pre-excites those sites relative to the rest of the ventricle and mechanically unloads the vulnerable region. Pre-excitation pacing therapy to unload a vulnerable region may be implemented by pacing the ventricles at a single site in proximity to the vulnerable region or by pacing at multiple ventricular sites in such proximity. In the latter case, the pacing pulses may be delivered to the multiple sites simultaneously or in a defined pulse output sequence. The single-site or multiple site pacing may be performed in accordance with a bradycardia pacing algorithm such as an inhibited demand mode or a triggered mode.

As described below, an implantable cardiac pacing device may be configured with one or more pacing electrodes disposed at a pre-excitation pacing site(s) in proximity to the vulnerable region. The device may then be programmed to operate in a vulnerable region unloading mode that delivers pre-excitation pacing pulses to the vulnerable region in accordance with a programmed pacing mode. The pre-excitation pacing relieves stress on the vulnerable region and reduces any ischemia that may be present by decreasing the metabolic demand of the region. The device may be programmed to operate in the vulnerable region unloading mode continuously or intermittently. In the latter case, the device may revert to a normal mode when the vulnerable region unloading mode terminates that may include any type of pacing (e.g., bradycardia or cardiac resynchronization pacing) or no pacing at all. The device may then switch from the normal mode to the vulnerable region unloading mode in accordance with one or more entry conditions such as: 1) actuation of a patient-operated switch that the patient may operate when angina occurs, 2) receipt of a telemetry command to initiate the mode, and 3) detection of the presence of myocardial ischemia by the device in accordance with a sensed variable that is correlated with the presence of myocardial ischemia. Examples of sensed variables reflective of myocardial ischemia include features derived from sensed cardiac electrical activity and/or, in a patient with demand ischemia, variables related to exertion level such as heart rate, minute ventilation, and activity level. The vulnerable region unloading mode may also be caused to terminate upon detection of one or more specified events or conditions, referred to as exit conditions. Such exit conditions could include, for example, non-detection of the presence of myocardial ischemia, a lapsed time interval, actuation of a patient-operated switch, and receipt of a telemetry command to terminate the mode.

In order for pre-excitation pacing to cause early contraction of a paced region relative to other regions, the latter regions should not be excited by intrinsic excitation conducted from the AV node. When the vulnerable region unloading mode delivers pre-excitation pacing in an atrial tracking or AV sequential pacing mode, the AV delay interval should be selected to be short enough relative to the patient's intrinsic AV interval that depolarization spreads beyond the pre-excited site and excites the rest of the myocardium without interference from intrinsic excitation. The shorter the AV delay interval is relative to the patient's intrinsic AV interval, the more the paced site is pre-excited. In one embodiment, the device is configured to dynamically shorten the AV delay interval in the vulnerable region unloading mode in accordance with a sensed variable that is correlated with the presence of myocardial ischemia such as described above in order to provide more stress reducing pre-excitation as it is needed. For example, the AV delay interval could be shortened in accordance with measured heart rate or exertion level. Shortening the AV delay interval in this manner also compensates for the physiological shortening of the patient's intrinsic AV interval that occurs with increasing heart rate.

Another use of pre-excitation pacing in the treatment of myocardial ischemia is to intentionally stress a vulnerable region by pacing at a site(s) remote from the vulnerable region. As described above, such pacing causes increased mechanical stress to the vulnerable region by delaying its contraction during systole relative to other regions. Intermittently stressing the vulnerable region causes a low level of myocardial ischemia in the region in a patient with demand ischemia, thereby promoting angiogenesis and possibly preconditioning the vulnerable region to better withstand the effects of a subsequent ischemic episode. Accordingly, the device may be configured to intermittently switch from a normal mode or vulnerable region unloading mode to a vulnerable region loading mode that delivers pre-excitation pacing to a site(s) remotely located from the vulnerable region. Such pre-excitation pacing may be delivered with a shortened or dynamically shortened AV delay interval as described above to facilitate the pre-excitation. Intermittent switching to the vulnerable region loading mode may be controlled in accordance with one or more entry conditions and one or more exit conditions, where such entry and exit conditions may include lapsed time intervals, heart rate, activity level as measured by an accelerometer, and minute ventilation. Since the vulnerable region loading mode is designed to produce low level myocardial ischemia, it is desirable for it to only be employed when the patient is at rest and not experiencing an ischemic episode by reason of either increased metabolic demand or decreased blood supply. For example, an entry condition for entering the vulnerable region loading mode could be the measured heart rate and/or exertion level being below some specified threshold value, and an exit condition for terminating the vulnerable region loading mode could be the measured heart rate and/or exertion level being above some specified threshold value. Additional entry and exit conditions could be lapsed time intervals based upon a defined schedule so that the vulnerable region loading mode is only entered at certain times of the day and/or is limited in duration.

Exemplary Implantable Device

FIG. 1 shows an implantable cardiac device 100 for delivering pre-excitation therapy to a vulnerable region as well as possibly other types of pacing therapy. Implantable pacing devices are typically placed subcutaneously or submuscularly in a patient's chest with leads threaded intravenously into the heart to connect the device to electrodes disposed within a heart chamber that are used for sensing and/or pacing of the chamber. Electrodes may also be positioned on the epicardium by various means. A programmable electronic controller causes the pacing pulses to be output in response to lapsed time intervals and/or sensed electrical activity (i.e., intrinsic heart beats not as a result of a pacing pulse). The device senses intrinsic cardiac electrical activity through one or more sensing channels, each of which incorporates one or more of the electrodes. In order to excite myocardial tissue in the absence of an intrinsic beat, pacing pulses with energy above a certain threshold are delivered to one or more pacing sites through one or more pacing channels, each of which incorporates one or more of the electrodes. FIG. 1 shows the exemplary device having two leads 200 and 300, each of which is a multi-polar (i.e., multi-electrode) lead having electrodes 201-202 and 301-304, respectively. The electrodes 201-202 are disposed in the right ventricle in order to excite or sense right ventricular and/or septal regions, while the electrodes 301-304 are disposed in the coronary sinus in order to excite or sense regions of the left ventricle. If a vulnerable region VR were located in the apical region of the left ventricle, pre-excitation pacing in a vulnerable region unloading mode could be delivered via electrodes 303 and 304 in a bipolar pacing configuration to unload the vulnerable region. Such pre-excitation pacing could be delivered, for example, as left ventricular-only pacing or as biventricular pacing with an offset such that the left ventricle is paced before the right. Conversely, in a vulnerable region loading mode, pre-excitation pacing could be delivered via electrodes 201 and 202 in a right ventricle-only pacing mode or electrodes 301 and 302 in a left ventricle-only or biventricular pacing mode in order to pre-excite a myocardial region remote from the vulnerable region. Other embodiments may use any number of electrodes in the form of unipolar and/or multi-polar leads in order to excite different myocardial sites. As explained below, once the device and leads are implanted, the pacing and/or sensing channels of the device may be configured with selected ones of the multiple electrodes in order to selectively pace or sense a particular myocardial site(s).

Figure 2:
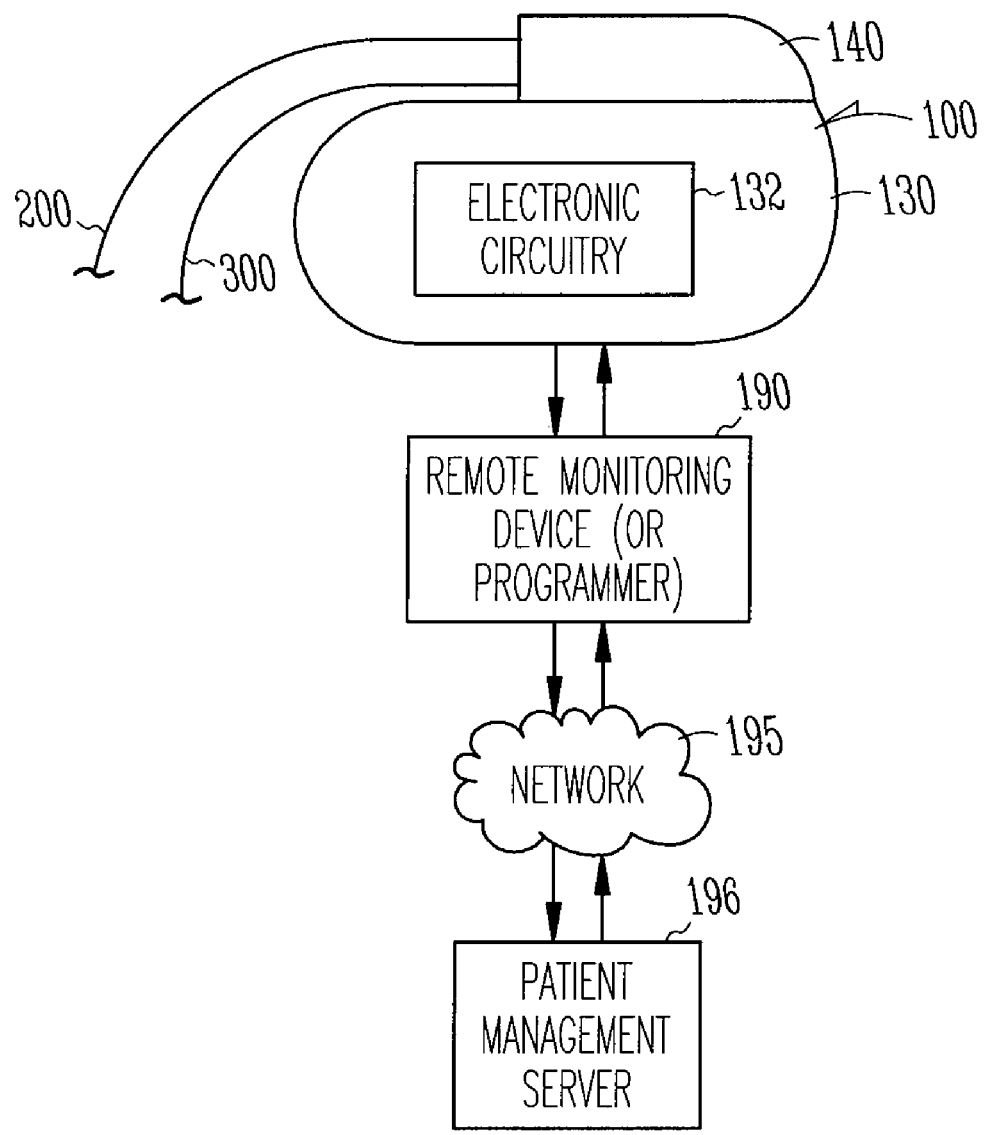
FIG. 2 shows the components of an exemplary device.

FIG. 2 shows the components of the implantable device 100 in more detail as well as an exemplary monitoring/programming system. The implantable device 100 includes a hermetically sealed housing 130 that is placed subcutaneously or submuscularly in a patient's chest. The housing 130 may be formed from a conductive metal, such as titanium, and may serve as an electrode for delivering electrical stimulation or sensing in a unipolar configuration. A header 140, which may be formed of an insulating material, is mounted on the housing 130 for receiving leads 200 and 300 which may be then electrically connected to pulse generation circuitry and/or sensing circuitry. Contained within the housing 130 is the electronic circuitry 132 for providing the functionality to the device as described herein which may include a power supply, sensing circuitry, pulse generation circuitry, a programmable electronic controller for controlling the operation of the device, and a telemetry transceiver capable of communicating with an external programmer or a remote monitoring device 190. An external programmer wirelessly communicates with the device 100 and enables a clinician to receive data and modify the programming of the controller. A remote monitoring device also communicates via telemetry with the device 100 and may be further interfaced to a network 195 (e.g., an internet connection) for communicating with a patient management server 196 that allows clinical personnel at remote locations to receive data from the remote monitoring device as well as issue commands. The controller may be programmed such when particular conditions are detected by the monitoring circuitry (such as when a measured parameter exceeds or falls below a specified limit value), the device transmits an alarm message to the remote monitoring device and to the patient management server to alert clinical personnel.

Figure 3:
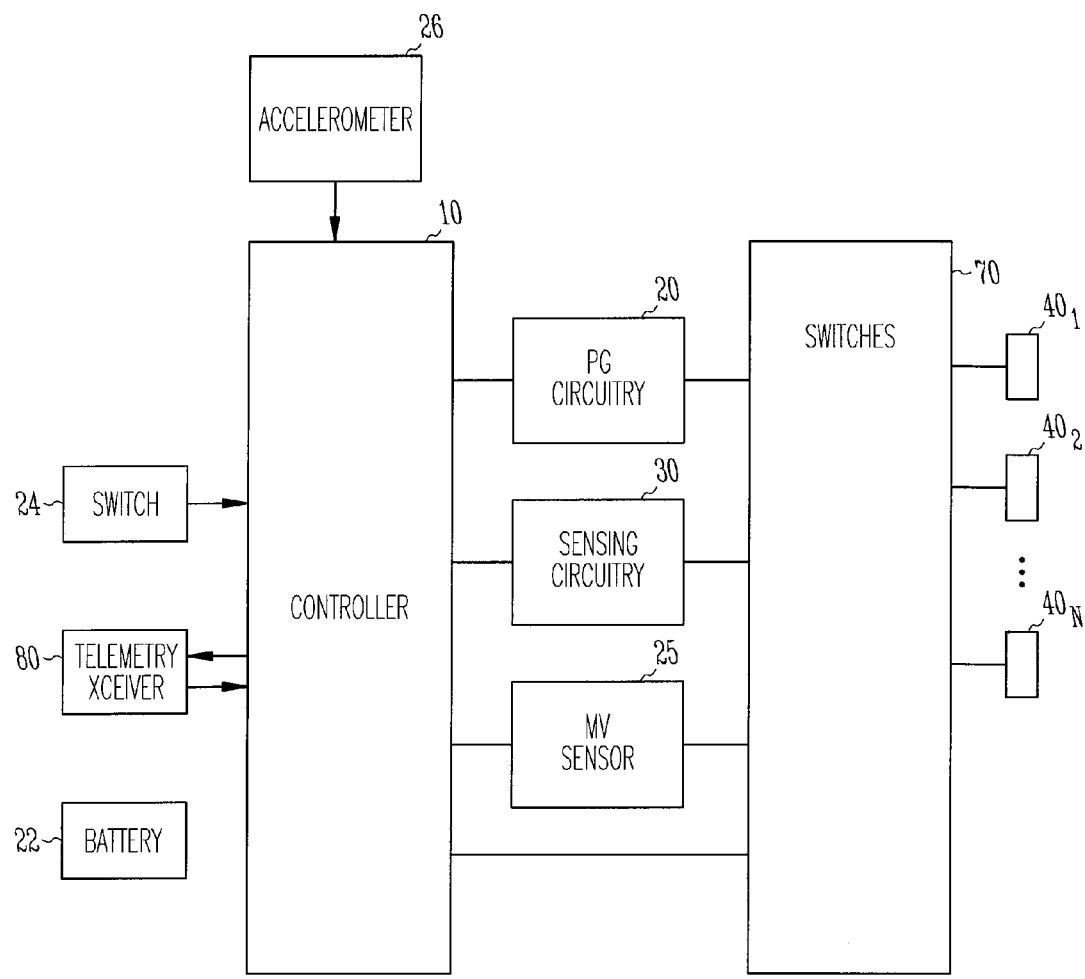
FIG. 3 is a block diagram of the electronic circuitry of an exemplary device.

A block diagram of the circuitry 132 is illustrated in FIG. 3. A battery 22 supplies power to the circuitry. The controller 10 controls the overall operation of the device in accordance with programmed instructions and/or circuit configurations. The controller may be implemented as a microprocessor-based controller and include a microprocessor and memory for data and program storage, implemented with dedicated hardware components such as ASICs (e.g., finite state machines), or implemented as a combination thereof. The controller also includes timing circuitry such as external clocks for implementing timers used to measure lapsed intervals and schedule events. As the term is used herein, the programming of the controller refers to either code executed by a microprocessor or to specific configurations of hardware components for performing particular functions. Interfaced to the controller are sensing circuitry 30 and pulse generation circuitry 20 by which the controller interprets sensing signals and controls the delivery of paces in accordance with a pacing mode. The sensing circuitry 30 receives atrial and/or ventricular electrogram signals from sensing electrodes and includes sensing amplifiers, analog-to-digital converters for digitizing sensing signal inputs from the sensing amplifiers, and registers that can be written to for adjusting the gain and threshold values of the sensing amplifiers. The pulse generation circuitry 20 delivers pacing pulses to pacing electrodes disposed in the heart and includes capacitive discharge pulse generators, registers for controlling the pulse generators, and registers for adjusting pacing parameters such as pulse energy (e.g., pulse amplitude and width). The device allows adjustment of the pacing pulse energy in order to ensure capture of myocardial tissue (i.e., initiating of a propagating action potential) by a pacing pulse. Myocardial sites in proximity to an ischemic region may be less excitable than normal and require an increased pacing energy in order to achieve capture. Pacing pulse energies for pre-exciting ischemic regions may be adjusted by programming the device via the telemetry interface in accordance with electrophysiological testing to determine an appropriate pacing pulse energy or may be adjusted automatically with an autocapture function such as described in U.S. patent application Ser. No. 11/427,517, filed on Jun. 29, 2006. The pulse generation circuitry may also include a shocking pulse generator for delivering a defibrillation/cardioversion shock via a shock electrode upon detection of a tachyarrhythmia. A telemetry transceiver 80 is interfaced to the controller which enables the controller to communicate with an external programmer and/or a remote monitoring unit. A magnetically or tactilely actuated switch 24 is also shown as interfaced to the controller to allow the patient to signal certain conditions or events to the implantable device.

A pacing channel is made up of a pulse generator connected to an electrode, while a sensing channel is made up of a sense amplifier connected to an electrode. Shown in the figure are electrodes $40_1$ through $40_N$ where N is some integer. The electrodes may be on the same or different leads and are electrically connected to a MOS switch matrix 70. The switch matrix 70 is controlled by the controller and is used to switch selected electrodes to the input of a sense amplifier or to the output of a pulse generator in order to configure a sensing or pacing channel, respectively. The device may be equipped with any number of pulse generators, amplifiers, and electrodes that may be combined arbitrarily to form sensing or pacing channels. The switch matrix 70 allows selected ones of the available implanted electrodes to be incorporated into sensing and/or pacing channels in either unipolar or bipolar configurations. A bipolar sensing or pacing configuration refers to the sensing of a potential or output of a pacing pulse between two closely spaced electrodes, where the two electrodes are usually on the same lead (e.g., a ring and tip electrode of a bipolar lead or two selected electrodes of a multi-polar lead). A unipolar sensing or pacing configuration is where the potential sensed or the pacing pulse output by an electrode is referenced to the conductive device housing or another distant electrode.

The device illustrated in FIG. 3 may be configured with multiple sensing and/or pacing channels that may be either atrial or ventricular channels depending upon the location of the electrode. The device is therefore capable of delivering single-site or multiple site ventricular pre-excitation pacing for purposes of stress reduction/augmentation as well as conventional pacing. The switch matrix allows particular myocardial sites to be pre-excited for purposes of stress reduction or augmentation by selecting the appropriately disposed electrode(s) to be incorporated into a pacing channel used to deliver pre-excitation pacing. Configuration of pacing and sensing channels may be performed via an external programmer communicating through the telemetry interface as well as automatically by the device when switching to or from different pacing modes.

Pre-excitation pacing may be delivered as single-site pacing, biventricular pacing where one of the ventricles is pre-excited relative to the other as determined by a programmed biventricular offset interval, or delivered as multi-site ventricular pacing. In the case where the pre-excitation pacing is delivered at multiple sites, the sites may be paced simultaneously or in accordance with a particular pulse output sequence that specifies the order and timing in which the sites are to be paced during a single beat. When an electrogram signal in an atrial or ventricular sensing channel exceeds a specified threshold, the controller detects an atrial or ventricular sense, respectively, which pacing algorithms may employ to trigger or inhibit pacing. The controller is capable of operating the device in a number of programmed modes where a programmed mode defines how pacing pulses are output in response to sensed events and expiration of time intervals. Pre-excitation pacing of one or more ventricular sites in proximity to, or remote from, a vulnerable region may be delivered in conjunction with a bradycardia pacing mode, which refers to a pacing algorithm that enforces a certain minimum heart rate, and may include or not include pacing pulses delivered to the atria or ventricles for other purposes (e.g., treatment of bradycardia). Inhibited demand bradycardia pacing modes utilize escape intervals to control pacing in accordance with sensed intrinsic activity. In an inhibited demand ventricular pacing mode, the ventricle is paced during a cardiac cycle only after expiration of a defined escape interval during which no intrinsic beat by the chamber is detected. For example, a ventricular escape interval can be defined between ventricular events so as to be restarted with each ventricular sense or pace, referred to as a lower rate interval (LRI). The inverse of this escape interval is the minimum rate at which the pacemaker will allow the ventricles to beat, sometimes referred to as the lower rate limit (LRL). Paces may also be delivered in a rate-adaptive pacing mode where the escape intervals are modified in accordance with a measured exertion level such as with accelerometer 26 or minute ventilation sensor 25. In atrial tracking and AV sequential pacing modes, another ventricular escape interval is defined between atrial and ventricular events, referred to as the atrio-ventricular or AV interval. The atrio-ventricular interval is triggered by an atrial sense or pace and stopped by a ventricular sense or pace. A ventricular pace is delivered upon expiration of the atrio-ventricular interval if no ventricular sense occurs before the expiration. Delivering pre-excitation pacing with a shortened AV interval relative to the patient's intrinsic AV interval (e.g., 30-80% of the intrinsic interval) facilitates pre-excitation by allowing the depolarization to spread beyond the pre-excited site and excite the rest of the myocardium without interference from intrinsic excitation.

The implantable device may also incorporate autocapture, autothreshold, and reconfiguration functionality described in U.S. patent application Ser. No. 11/427,517, filed on Jun. 29, 2006, which are especially useful for the delivery of pre-excitation pacing to a vulnerable region because the excitability characteristics of a vulnerable region may change over time. The device thus may be configured to automatically adjust pre-excitation pacing pulse energies and/or pre-excitation pacing sites in order maintain capture by the pre-excitation pacing pulses. In order to determine whether or not a pacing pulse has achieved capture, a capture verification test is performed in which an evoked response to the pre-excitation pacing pulse detected. An evoked response sensing channel is configured using the switch matrix to select an appropriate electrode which may be the same electrode used to deliver the pacing pulse or another electrode disposed near the pacing site. Verifying capture by the pacing pulse involves comparing the evoked response electrogram signal following the pace to a predetermined threshold, which may be performed by the controller or other dedicated circuitry. If the evoked response electrogram signal exceeds the threshold, capture is presumed to have occurred. Upon detection of capture failure, or in order to determine a minimum pacing energy, an autothreshold procedure may be performed by the device in which a minimum pacing threshold is determined. The pacing pulse energy is then adjusted accordingly to match the determined minimum pacing threshold with an appropriate safety margin. Automatic pacing electrode reconfiguration, entailing changing pacing sites until one is found for which capture is possible, may be performed upon detection of a loss of capture and when the autocapture function is unable to adjust the pacing pulse energy for a particular pacing site to a level adequate to regain capture using the available pacing pulse amplitudes and widths supported by the device. The pacing electrode reconfiguration algorithm can also be performed periodically or upon command. Such reconfiguration may be performed in accordance with a pre-programmed ordered list of the available pacing electrodes that lists the electrodes in a preferred order of use as determined by clinical testing in order to ensure that the reconfiguration algorithm selects the most optimum pacing location for pre-excitation pacing.

Detection of Myocardial Ischemia

When the blood supply to a region of the myocardium is compromised, the supply of oxygen and other nutrients can become inadequate for enabling the metabolic processes of the cardiac muscle cells to maintain their normal polarized state. An ischemic region of the heart therefore becomes abnormally depolarized during at least part of the cardiac cycle and causes a current to flow between the ischemic region and the normally polarized regions of the heart, referred to as a current of injury. A current of injury may be produced by an infarcted region that becomes permanently depolarized or by an ischemic region that remains abnormally depolarized during all or part of the cardiac cycle. Ischemia and infarction can also affect the magnitude of depolarization and the velocity at which it travels through the myocardium. All of these effects result in abnormal changes in the electrical potentials produced by cardiac excitation as reflected by either a surface electrocardiogram or an intracardiac electrogram. The device may therefore be configured to detect the presence of myocardial ischemia from one or more sensed variables related to cardiac electrical activity.

The device may be configured to detect cardiac ischemia from a morphology analysis of an electrogram collected during an intrinsic or a paced beat, the latter sometimes referred to as an evoked response. As aforesaid, a current of injury results in an abnormal change in the electrical potentials measured by an intracardiac electrogram. If the abnormal depolarization in the ventricles lasts for the entire cardiac cycle, a zero potential is measured only when the rest of the ventricular myocardium has depolarized, which corresponds to the time between the end of the QRS complex and the T wave in an electrogram and is referred to as the ST segment. After repolarization of the ventricles, marked by the T wave in an electrogram, the measured potential is influenced by the current of injury and becomes shifted, either positively or negatively depending upon the location of the ischemic or infarcted region, relative to the ST segment. Traditionally, however, it is the ST segment that is regarded as shifted when an abnormal current of injury is detected by an electrogram or electrocardiogram. A current injury produced by an ischemic region that does not last for the entire cardiac cycle may only shift part of the ST segment, resulting in an abnormal slope of the segment. A current of injury may also be produced when ischemia causes a prolonged depolarization in a ventricular region which results in an abnormal T wave as the direction of the wave of repolarization is altered. In order for the device to detect a change in an electrogram indicative of ischemia, a recorded electrogram is analyzed and compared with a reference electrogram, which may either be a complete recorded electrogram or particular reference values representative of an electrogram. Because certain patients may always exhibit a current of injury in an electrogram (e.g., due to CAD or as a result of electrode implantation), the controller may be programmed to detect ischemia by looking for an increased current of injury in the recorded electrogram as compared with the reference electrogram, where the latter may or may not exhibit a current of injury. One way to look for an increased current of injury in the recorded electrogram is to compare the ST segment amplitude and/or slope with the amplitude and slope of a reference electrogram. Various digital signal processing techniques may be employed for the analysis, such as using first and second derivatives to identify the start and end of an ST segment. Other ways of looking for a current injury may involve, for example, cross-correlating the recorded and reference electrograms to ascertain their degree of similarity. The electrogram could be implicitly recorded in that case by passing the electrogram signal through a matched filter that cross-correlates the signal with a reference electrogram. The ST segment could also be integrated, with the result of the integration compared with a reference value to determine if an increased current of injury is present.

As mentioned previously, other sensed variables may also be indicative of the presence of myocardial ischemia, especially in patients with exertional angina. The device may therefore be programmed to detect the presence of myocardial ischemia from sensed variables such as heart rate, activity level, local cardiac motion, local tissue impedance, and minute ventilation, either in addition to or instead of the techniques discussed above based upon cardiac electrical activity. To add specificity to the detection scheme, for example, the device may be programmed to detect myocardial ischemia only when a current of injury is detected and the patient's heart rate and/or exertion level is above a specified threshold value.

Exemplary Implementations

In order to provide pre-excitation therapy as described above to a myocardial region vulnerable to becoming ischemic, the region must be identified anatomically so that one or more pacing electrodes can be placed in proximity thereto. An area of ischemia can be identified by a number of means, including ultrasonic imaging, PET scans, thallium scans, and MRI perfusion scans. Stress testing may be employed to induce myocardial ischemia in a patient with demand ischemia. A myocardial region identified as either ischemic or vulnerable to becoming ischemic is deemed to be a vulnerable region that can be mechanically loaded or unloaded with pre-excitation pacing therapy. After implantation and appropriate placement of electrodes, the device may then be programmed to be configured with appropriate sensing and pacing channels to deliver pre-excitation pacing to one or more sites in proximity to, and/or remote from, the identified vulnerable region accordance with a particular pacing mode.

An exemplary implantable pacing device is equipped with one or more leads having first and second electrodes that can be placed at different pacing sites. In an exemplary electrode placement, the first electrode is disposed near a ventricular region vulnerable to ischemia so that a pacing pulse from the first electrode unloads the vulnerable region during systole as compared with an intrinsic beat, and the second electrode is disposed near a ventricular region remote from the vulnerable region so that a pacing pulse from the second electrode loads the vulnerable region during systole as compared with an intrinsic beat. The device may be configured to operate in a vulnerable region unloading mode that delivers pacing pulses through a pacing channel configured with the first electrode and to intermittently operate in a vulnerable region loading mode that delivers pacing pulses through a pacing channel configured with the second electrode.

The device may also be equipped with one or more sensors for sensing a variable that can be correlated with the occurrence of myocardial ischemia and programmed to detect the presence or absence of myocardial ischemia in accordance with the sensed variable. In various embodiments, the sensor(s) may be a cardiac sensing channel for recording electrograms and measuring heart rate, an accelerometer for measuring activity level or local cardiac motion, an impedance sensor sensitive to local changes in tissue impedance that occur during ischemia, and/or a minute ventilation sensor. The device may then be configured to intermittently switch to the vulnerable region loading mode according to a defined schedule but to switch to the vulnerable region loading mode only if the sensed variable indicates the absence of myocardial ischemia. For example, the device may sense the patient's exertion level (e.g., as reflected by heart rate, activity level, and/or minute ventilation) and be configured to intermittently switch to the vulnerable region loading mode but to switch to the vulnerable region loading mode only if the sensed variable is within a specified range.

Figure 4:
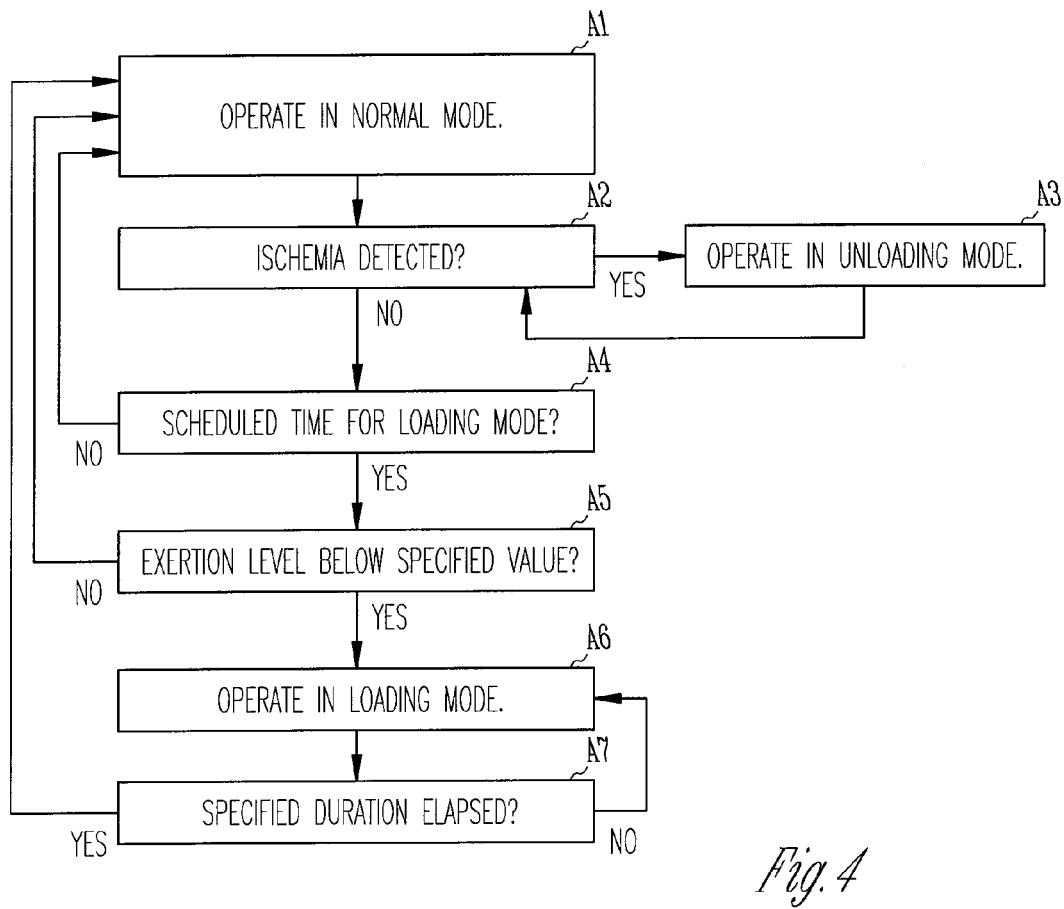
FIG. 4 illustrates an exemplary algorithm for switching between a normal mode and vulnerable region unloading and loading modes.

The device could also be configured to operate in a normal mode when not operating in either the vulnerable region unloading or loading modes, where the normal mode may or may not deliver pacing therapy. In one embodiment, for example, the device is equipped with a third electrode adapted for disposition near a ventricular region apart from the locations of the first and second electrodes, and the controller is programmed to operate in a normal mode that delivers pacing pulses through a pacing channel configured with the third electrode. The controller is then programmed to switch to the vulnerable region unloading mode whenever the sensed variable indicates the presence of myocardial ischemia and operate intermittently in either the vulnerable region loading mode or the normal mode whenever the sensed variable indicates the absence of myocardial ischemia. The device could also be configured to switch from the normal mode to the vulnerable region unloading mode if the sensed variable indicates the presence of myocardial ischemia. FIG. 4 illustrates an example algorithm that could be executed by the controller to switch between the normal mode and the vulnerable region unloading or loading modes. At step A1, the device operates in the normal mode, which may entail delivering some kind of pacing therapy (e.g., bradycardia or resynchronization pacing) or delivering no pacing at all. At step A2, the device checks for the presence of ischemia. If myocardial ischemia is detected, the device operates in the vulnerable region unloading mode at step A3 for as long as the ischemia is present. If myocardial ischemia is not present, the device checks to see if it is time to switch to the vulnerable region loading mode at step A4. If so, the device determines at step A5 if the measured exertion level is below a specified value that indicates the patient is at rest. If the patient is at rest, the device operates in the vulnerable region loading mode at step A6 and remains in that mode until a specified duration has elapsed as determined at step A7.

In order to provide atrio-ventricular synchrony, the device may be configured to deliver pacing pulses in the vulnerable region unloading and/or vulnerable region loading modes in accordance with an atrial tracking or AV sequential pacing mode with a specified AV delay interval. To facilitate pre-excitation in either the unloading or loading mode, the AV delay interval should be set shorter than the measured intrinsic AV interval so that intrinsic excitation of the ventricle does not interfere with excitation from the pre-excitation pacing. For example, the AV delay interval may be set to be between 50 and 80% of the measured intrinsic AV interval. In one embodiment, the device is configured to measure the patient's intrinsic AV interval and set the AV delay interval automatically in accordance with the measurement.

Figure 5:
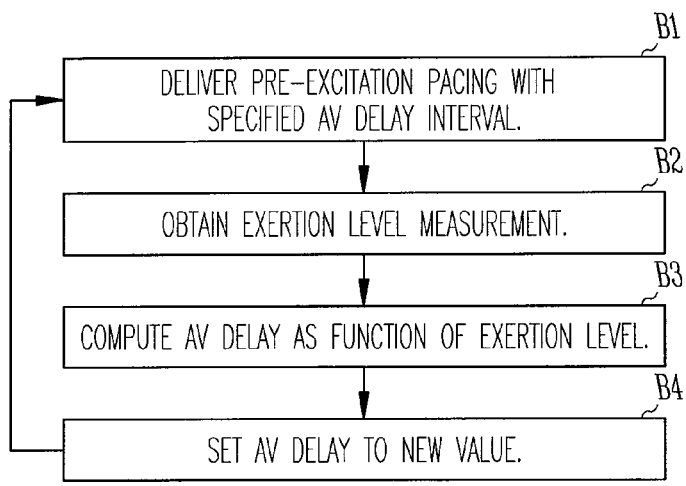
FIG. 5 illustrates an exemplary algorithm for dynamically varying an AV delay interval when delivering pre-excitation pacing.

The device may also be configured to dynamically adjust the AV delay interval to compensate for changes in the patient's intrinsic AV interval and/or adjust the amount of pre-excitation delivered in the vulnerable region unloading and/or loading modes. In this embodiment, the device may configured to adjust the AV delay interval in accordance with a sensed variable reflective of myocardial ischemia and/or the patient's exertion level such as heart rate, activity level, and/or minute ventilation. FIG. 5 illustrates an example algorithm that could be executed by the controller while delivering pre-excitation pacing in the vulnerable region unloading or loading modes. At step B1, the device delivers pre-excitation pacing with a specified AV delay interval. At step B2, the device obtains a measurement of the patient's exertion level, which may be an instantaneous or an average measurement. At step B3, the AV delay interval is computed as a function of the exertion level measurement which may be implemented, for example, as a look-up table. Under normal circumstances, the AV delay interval will be decreased as the measured exertion level increases and vice-versa. At step B4, the AV delay interval is set to the computed value, and a return is made to step B1 to continue pre-excitation pacing with the new AV delay interval.

In another embodiment, the patient is provided with a means for switching the device to the vulnerable region loading mode, to the vulnerable region unloading mode upon experiencing symptoms of myocardial ischemia, and/or to a normal mode. Such a means, for example, may be a patient-operated switch interfaced to the device controller such as a magnetically-actuated or tactilely-actuated switch. The patient may also be provided with a means for communicating to the device via telemetry, such as from a remote monitor, in order to issue a command to switch to a selected mode.

The invention has been described in conjunction with the foregoing specific embodiments. It should be appreciated that those embodiments may also be combined in any manner considered to be advantageous. Also, many alternatives, variations, and modifications will be apparent to those of ordinary skill in the art. Other such alternatives, variations, and modifications are intended to fall within the scope of the following appended claims.

What is claimed is:

1. A method, comprising:
   identifying a vulnerable ventricular region in a patient that is predisposed to becoming ischemic;
   implanting a cardiac pacing device having first and second electrodes;
   implanting the first electrode near the ventricular region vulnerable to ischemia so that a pacing pulse from the first electrode unloads the vulnerable region during systole as compared with an intrinsic beat;
   implanting the second electrode near a ventricular region remote from the vulnerable region so that a pacing pulse from the second electrode loads the vulnerable region during systole as compared with an intrinsic beat;
   configuring the device to operate in a vulnerable region unloading mode that delivers pacing pulses in accordance with an atrial tracking or AV sequential pacing mode with a specified AV delay interval through a pacing channel configured with the first electrode, a vulnerable region loading mode that delivers pacing pulses in accordance with an atrial tracking or AV sequential pacing mode with a specified AV delay interval through a pacing channel configured with the second electrode, or a normal mode that delivers no pacing pulses to either the first or second electrodes;
   configuring the device to sense a variable related to the patient's exertion level;
   configuring the device to sense a variable that can be correlated with the occurrence of myocardial ischemia and to detect the presence or absence of myocardial ischemia in accordance with the sensed variable;
   configuring the device to intermittently switch from the normal mode to the vulnerable region loading mode according to a defined schedule if the sensed variable indicates the absence of myocardial ischemia;
   configuring the device to switch from either the normal mode or the vulnerable region loading mode to the vulnerable region unloading mode if the sensed variable indicates the presence of myocardial ischemia;
   configuring the device to dynamically shorten the AV delay in accordance with measured exertion level in the vulnerable region loading mode; and,
   configuring the device to dynamically shorten the AV delay in accordance with the sensed variable correlated with ischemia in the vulnerable region unloading mode.

2. The method of claim 1 further comprising:
   configuring the device to measure the patient's intrinsic AV interval;
   configuring the device to deliver pacing pulses in both the vulnerable region unloading and vulnerable region loading modes with a specified AV delay interval shorter than the measured intrinsic AV interval.

3. The method of claim 1 further comprising:
   configuring the device to switch to the vulnerable region loading mode only if the sensed variable related to exertion level is within a specified range.

4. The method of claim 1 further comprising:
implanting a third electrode near a ventricular region between the first and second electrodes; and,
configuring the device to deliver pacing pulses in the normal mode in accordance with an atrial tracking or AV sequential pacing mode with a specified AV delay interval longer than that used for the vulnerable region unloading and vulnerable region loading modes.

5. The method of claim 1 further comprising setting the AV delay interval to be between 30% and 80% of the measured intrinsic AV interval.

6. The method of claim 3 further comprising providing a minute ventilation sensor and wherein the controller is configured to measure the patient's exertion level as a function of minute ventilation.

7. The method of claim 3 further comprising providing an accelerometer for measuring the patient's activity level and wherein the controller is configured to measure the patient's exertion level as a function of activity level.

8. The method of claim 1 further comprising providing a patient-operated switch for switching the device to the vulnerable region loading mode.

9. The method of claim 1 further comprising providing a patient-operated switch for switching the device to the vulnerable region unloading mode if the patient experiences symptoms of myocardial ischemia.

10. A cardiac device, comprising:
a controller for controlling the operation of the device;
a sense amplifier interfaced to the controller for receiving electrograms reflective of cardiac activity;
a pulse generator operable by the controller for generating pacing pulses;
a switch matrix operable by the controller for configuring sensing channels by connecting the sensing amplifier to a selected electrode and for configuring pacing channels by connecting the pulse generator to a selected electrode;
wherein the controller is programmed to configure a pacing channel for a vulnerable region unloading mode with a first electrode adapted for disposition near a vulnerable ventricular region that is predisposed to becoming ischemic;
wherein the controller is programmed to configure a pacing channel for a vulnerable region loading mode with a second electrode adapted for disposition remote from the vulnerable ventricular region;
wherein the controller is programmed to operate in a vulnerable region unloading mode that delivers pacing pulses in accordance with an atrial tracking or AV sequential pacing mode with a specified AV delay interval through a pacing channel configured with the first electrode, a vulnerable region loading mode that delivers pacing pulses in accordance with an atrial tracking or AV sequential pacing mode with a specified AV delay interval through a pacing channel configured with the second electrode, or a normal mode that delivers no pacing pulses to either the first or second electrodes;
an exertion level sensor interfaced to the controller for measuring a patient's exertion level;
an ischemia sensor interfaced to the controller for sensing a variable that can be correlated with the occurrence of myocardial ischemia and wherein the controller is programmed to detect the presence or absence of myocardial ischemia;
wherein the controller is programmed to intermittently switch from the normal mode to the vulnerable region loading mode according to a defined schedule if the sensed variable indicates the absence of myocardial ischemia;
wherein the controller is programmed to switch from either the normal mode or the vulnerable region loading mode to the vulnerable region unloading mode if the sensed variable indicates the presence of myocardial ischemia;
wherein the controller is programmed to dynamically shorten the AV delay in accordance with measured exertion level in the vulnerable region loading mode; and,
wherein the controller is programmed to dynamically shorten the AV delay in accordance with the sensed variable correlated with ischemia in the vulnerable region unloading mode.

11. The device of claim 10 wherein the ischemia sensor is a cardiac sensing channel and wherein the controller is programmed to detect the presence of myocardial ischemia if a current of injury is found in an electrogram.

12. The device of claim 10 wherein the ischemia sensor is a cardiac sensing channel and wherein the controller is programmed to detect the presence of myocardial ischemia by cross-correlating a recorded electrogram with a reference electrogram.

13. The device of claim 10 wherein the exertion level sensor is an accelerometer for measuring the patient's activity level.

14. The device of claim 10 wherein the exertion level sensor is a minute ventilation sensor.

15. The device of claim 10 wherein the controller is programmed to:
measure the patient's intrinsic AV interval; and,
deliver pacing pulses in both the vulnerable region unloading and vulnerable region loading modes with a specified AV delay interval shorter than the measured intrinsic AV interval.

16. The device of claim 10 wherein the controller is programmed to intermittently switch to the vulnerable region loading mode only if the measured exertion level is within a specified range.

17. The device of claim 10 wherein the controller is programmed to configure a pacing channel with a third electrode adapted for disposition near a ventricular region between the first and second electrodes and further programmed to deliver pacing pulses in the normal mode in accordance with an atrial tracking or AV sequential pacing mode with a specified AV delay interval longer than that used for the vulnerable region unloading and vulnerable region loading modes.

18. The device of claim 10 further comprising a patient-operated switch for switching the device to the vulnerable region loading mode.

19. The device of claim 10 further comprising a patient-actuated switch and wherein the controller is programmed to switch to the vulnerable region unloading mode if the patient-actuated switch is actuated.

* * * * *